(12) United States Patent
Kim et al.

(10) Patent No.: US 12,036,565 B2
(45) Date of Patent: Jul. 16, 2024

(54) ECO-FRIENDLY SMART BLOOD MODULATION DEVICE

(71) Applicants: Jin Wang Kim, Seoul (KR); Joung Ok Lee, Seoul (KR); Hyun-Ji Kim, Seoul (KR); Hyun Woo Kim, Seoul (KR)

(72) Inventors: Jin Wang Kim, Seoul (KR); Joung Ok Lee, Seoul (KR); Hyun-Ji Kim, Seoul (KR); Hyun Woo Kim, Seoul (KR)

(*) Notice: Subject to any disclaimer, the term of this patent is extended or adjusted under 35 U.S.C. 154(b) by 534 days.

(21) Appl. No.: 17/245,408

(22) Filed: May 26, 2021

(65) Prior Publication Data
US 2022/0111401 A1 Apr. 14, 2022

(30) Foreign Application Priority Data
Oct. 14, 2020 (KR) .................. 10-2020-0132968

(51) Int. Cl.
*B04B 5/10* (2006.01)
*A61L 2/00* (2006.01)
(Continued)

(52) U.S. Cl.
CPC .............. *B04B 5/10* (2013.01); *A61L 2/0047* (2013.01); *A61L 2/0052* (2013.01);
(Continued)

(58) Field of Classification Search
CPC ........ B04B 5/10; A61L 2/0047; A61L 2/0052; A61L 2/0058; A61L 2/0076; A61L 2/26;
(Continued)

(56) References Cited

U.S. PATENT DOCUMENTS 4,321,919 A    3/1982  Edelson
4,464,166 A *  8/1984  Edelson .............. A61M 1/3681
                                                    604/20
(Continued)

FOREIGN PATENT DOCUMENTS

CN      2231107 Y  *  7/1996
IL      150914 B   *  4/2014
(Continued)

OTHER PUBLICATIONS

Machine-generated Enlgish translation of JP 3782678, generated on Dec. 13, 2023.*
(Continued)

*Primary Examiner* — Fred Prince
(74) *Attorney, Agent, or Firm* — Sughrue Mion, PLLC

(57) ABSTRACT

A blood processing apparatus including a blood supply unit, a centrifuge, a light irradiation unit, a filtering device, and a blood collection unit, which is characterized in that blood is introduced into the centrifuge and centrifuged, the centrifuged blood is passed through a transparent tube provided in the light irradiation unit while being irradiated with light applied, from the outside of the transparent tube, by a light irradiation device configured to include an infrared lamp with a wavelength of 830±5 nm, a red light-emitting diode (LED) lamp with a wavelength of 635±6 nm, a blue LED lamp with a wavelength of 420±5 nm, a green LED lamp with a wavelength of 530±5 nm, a yellow LED lamp with a wavelength of 585±5 nm, and ultraviolet (UV) lamps, and the blood irradiated with the light is filtered using the filtering device and collected in the blood collection unit.

2 Claims, 13 Drawing Sheets

(51) Int. Cl.
*A61L 2/26* (2006.01)
*A61M 1/02* (2006.01)
*A61M 1/16* (2006.01)
*A61M 1/32* (2006.01)
*A61M 1/36* (2006.01)
*B01D 21/26* (2006.01)
*B01D 36/04* (2006.01)

(52) U.S. Cl.
CPC .......... *A61L 2/0058* (2013.01); *A61L 2/0076* (2013.01); *A61L 2/26* (2013.01); *A61M 1/0259* (2013.01); *A61M 1/0272* (2013.01); *A61M 1/0281* (2013.01); *A61M 1/1698* (2013.01); *A61M 1/32* (2013.01); *A61M 1/3681* (2013.01); *A61M 1/3687* (2013.01); *A61M 1/3693* (2013.01); *B01D 21/262* (2013.01); *B01D 36/045* (2013.01); *A61L 2202/11* (2013.01); *A61L 2202/122* (2013.01); *A61L 2202/16* (2013.01); *A61L 2202/22* (2013.01); *A61M 1/3678* (2014.02); *A61M 1/3683* (2014.02); *A61M 2205/058* (2013.01)

(58) Field of Classification Search
CPC .......... A61L 2202/11; A61L 2202/122; A61L 2202/16; A61L 2202/22; A61M 1/0259; A61M 1/0272; A61M 1/0281; A61M 1/1698; A61M 1/32; A61M 1/3681; A61M 1/3687; A61M 1/3693; A61M 1/3678; A61M 1/3683; A61M 2205/058; B01D 21/262; B01D 36/045
USPC ....... 210/251, 259, 645, 646, 748.02, 748.1, 210/748.11, 748.13, 748.55, 781, 782, 210/748.15
See application file for complete search history.

(56) References Cited

U.S. PATENT DOCUMENTS

| | | | |
|---|---|---|---|
| 9,199,026 | B2* | 12/2015 | Greenberg .............. A61M 1/16 |
| 2011/0251544 | A1* | 10/2011 | Felder ................. A61M 1/3687 422/44 |
| 2013/0178834 | A1* | 7/2013 | Greenberg .......... A61M 1/3606 435/5 |
| 2019/0344008 | A1* | 11/2019 | Igarashi .......... A61M 1/362265 |

FOREIGN PATENT DOCUMENTS

| | | | |
|---|---|---|---|
| JP | 2000-93510 | A * | 4/2000 |
| JP | 3782678 | B2 * | 6/2006 |
| JP | 2008-246200 | A | 10/2008 |
| JP | 2016-055104 | A | 4/2016 |
| KR | 1020060071365 | A | 6/2006 |
| KR | 10-0915559 | B1 | 9/2009 |
| KR | 1020090105086 | A | 10/2009 |
| KR | 1020180022721 | A | 3/2018 |
| KR | 1020190017747 | A | 2/2019 |
| WO | WO 91/12831 | A1 * | 9/1991 |
| WO | WO 02/12127 | A2 * | 2/2002 |
| WO | WO 03/086479 | A1 * | 10/2003 |

OTHER PUBLICATIONS

Machine-generated Enlgish translation of JP 2000-93510, generated on Dec. 13, 2023.*

Machine-generated Enlgish translation of CN 2231107, generated on Dec. 13, 2023.*

Machine-generated Enlgish translation of WO 91/12831, generated on Dec. 13, 2023.*

* cited by examiner

Molecular formula of ALA

5-Aminolevulinic acid HCl 98% > 5-ALA

Molecular structure of G-CSF

ECO-FRIENDLY SMART BLOOD MODULATION DEVICE

CROSS-REFERENCE TO RELATED APPLICATION

This application claims priority to and the benefit of Korean Patent Application No. 10-2020-0132968, filed Oct. 14, 2020, the disclosure of which is incorporated herein by reference in its entirety.

BACKGROUND

1. Field of the Invention

The present invention relates to an eco-friendly smart blood modulation device for improving blood conditions using centrifugation and light irradiation.

2. Discussion of Related Art

Blood is produced in the bone marrow in the bones, and our body holds four to six liters of blood. Blood is circulated through arteries, capillaries, and veins by heartbeats. Blood carries oxygen, nutrients, and waste products and protects our body from diseases such as bacterial infections through white blood cells, antibodies, and the like. Blood includes blood cells and plasma components, and is produced as a result of the differentiation of hematopoietic stem cells of the bone marrow into red blood cells, white blood cells, and platelets. Plasma is mostly formed of water and contains protein components, chemicals, electrolytes, and the like.

In addition to performing the basic function of delivering oxygen and nutrients to various parts of the body, blood performs various tasks to regulate body temperature and maintain a constant amount of water or electrolyte concentration required by tissue cells. Immune substances, such as white blood cells in the blood, protect our body from external bacteria and perform a function of removing health threats such as cancer that occur in the human body.

Therefore, it can be said that the immune function of blood is an essential factor for a healthy body. Since blood only carries immune substances such as white blood cells and does not produce immune substances, it is not well known how to improve immune function at the blood level.

RELATED-ART DOCUMENT

Patent Document (Patent Document 1) Korean Patent Registration No. 10-0915559

SUMMARY OF THE INVENTION

As a result of making extensive efforts to find an effective way to improve the immune function of blood, the present inventors have found that it is possible to improve the immune function of blood through the centrifugation and light irradiation of the blood, and thereby completed the present invention.

Therefore, the present invention is directed to providing an eco-friendly smart blood modulation device capable of safely and effectively improving the immune function of blood.

One aspect of the present invention provides a blood processing apparatus, which includes a blood supply unit, a centrifuge, a light irradiation unit, a filtering device, and a blood collection unit and is characterized in that blood supplied from the blood supply unit is introduced into the centrifuge and centrifuged, the centrifuged blood is passed through a transparent tube provided in the light irradiation unit while being irradiated with light applied, from the outside of the transparent tube, by a light irradiation device configured to include an infrared lamp with a wavelength of $830\pm5$ nm, a red light-emitting diode (LED) lamp with a wavelength of $635\pm6$ nm, a blue LED lamp with a wavelength of $420\pm5$ nm, a green LED lamp with a wavelength of $530\pm5$ nm, a yellow LED lamp with a wavelength of $585\pm5$ nm, and one or more ultraviolet (UV) lamps selected from among UV-A and UV-B lamps, and the blood irradiated with the light is filtered using the filtering device and collected in the blood collection unit.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Hereinafter, exemplary embodiments of the present invention will be described in detail with reference to the accompanying drawings. In describing the present invention, when it is determined that a detailed description of a related known function and configuration may unnecessarily obscure the gist of the present invention, the description will be omitted.

The following descriptions and drawings illustrate specific embodiments so that those skilled in the art can easily implement the described apparatus and method. Other embodiments may include structurally and logically different variations. Individual components and functions may generally be selected unless explicitly required, and the sequence of processes may be varied. Parts and features of some embodiments may be included in or replaced by other embodiments.

Figure 1:
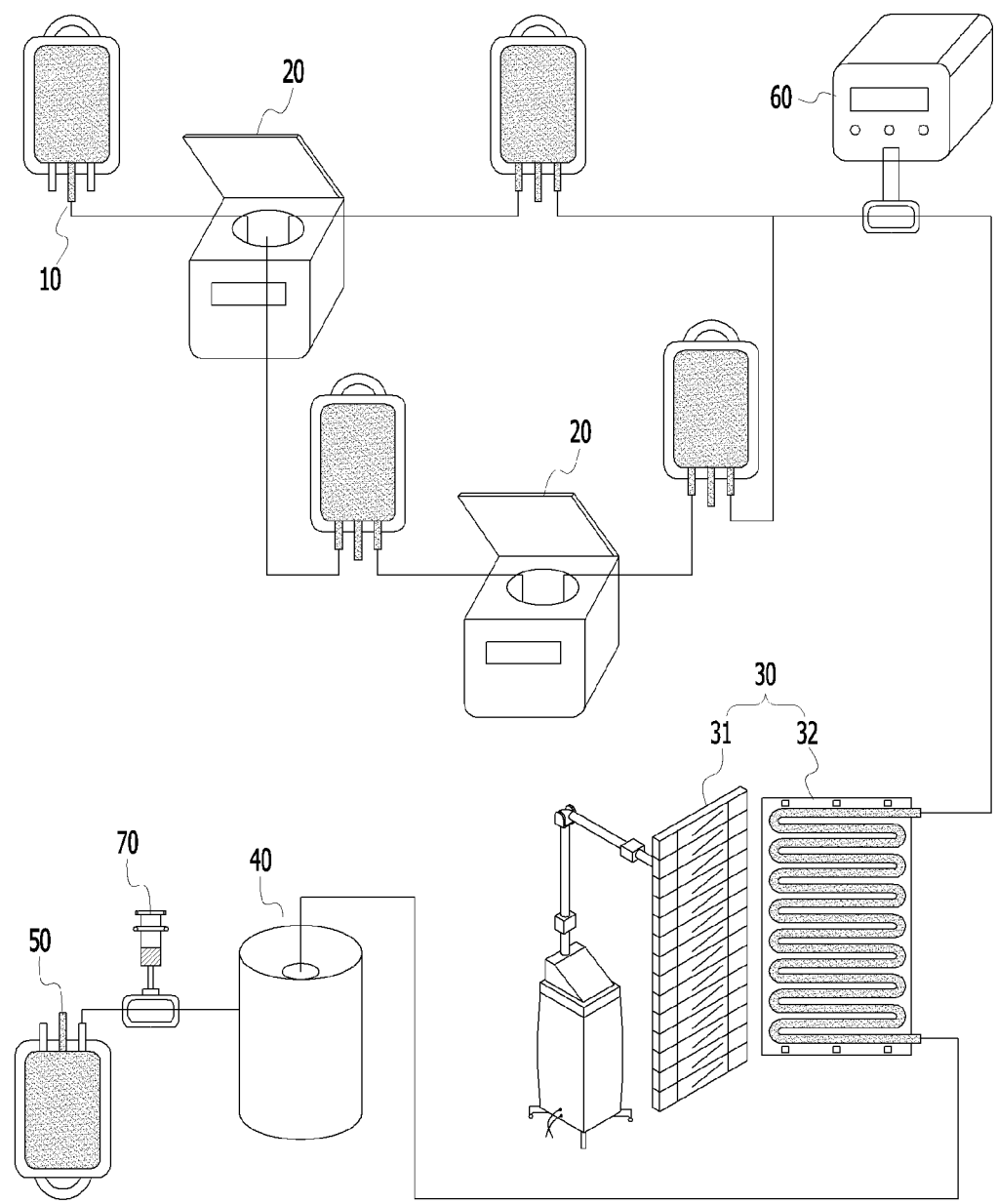
FIGS. 1 and 2 are structural diagrams of a blood processing apparatus of the present invention.
Figure 2:
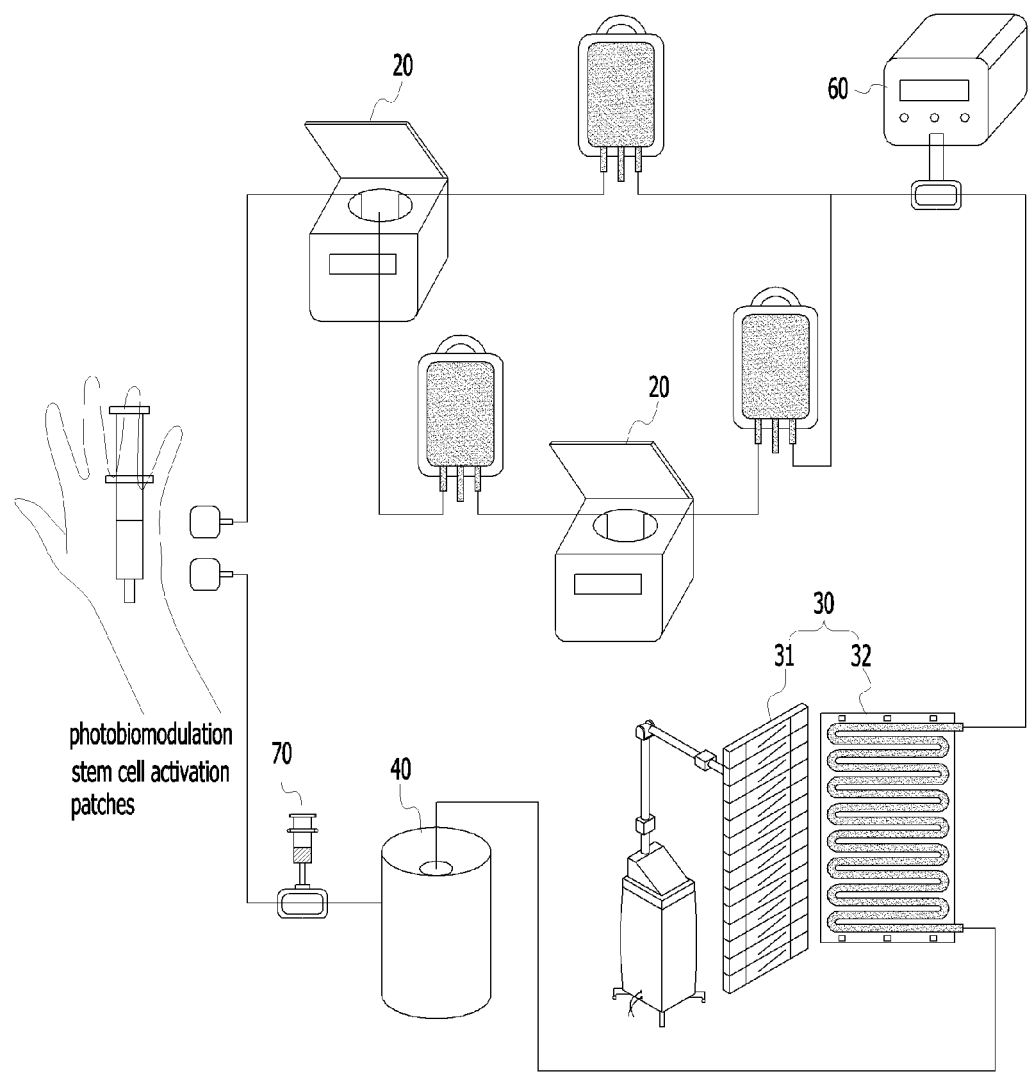
Figure 3:
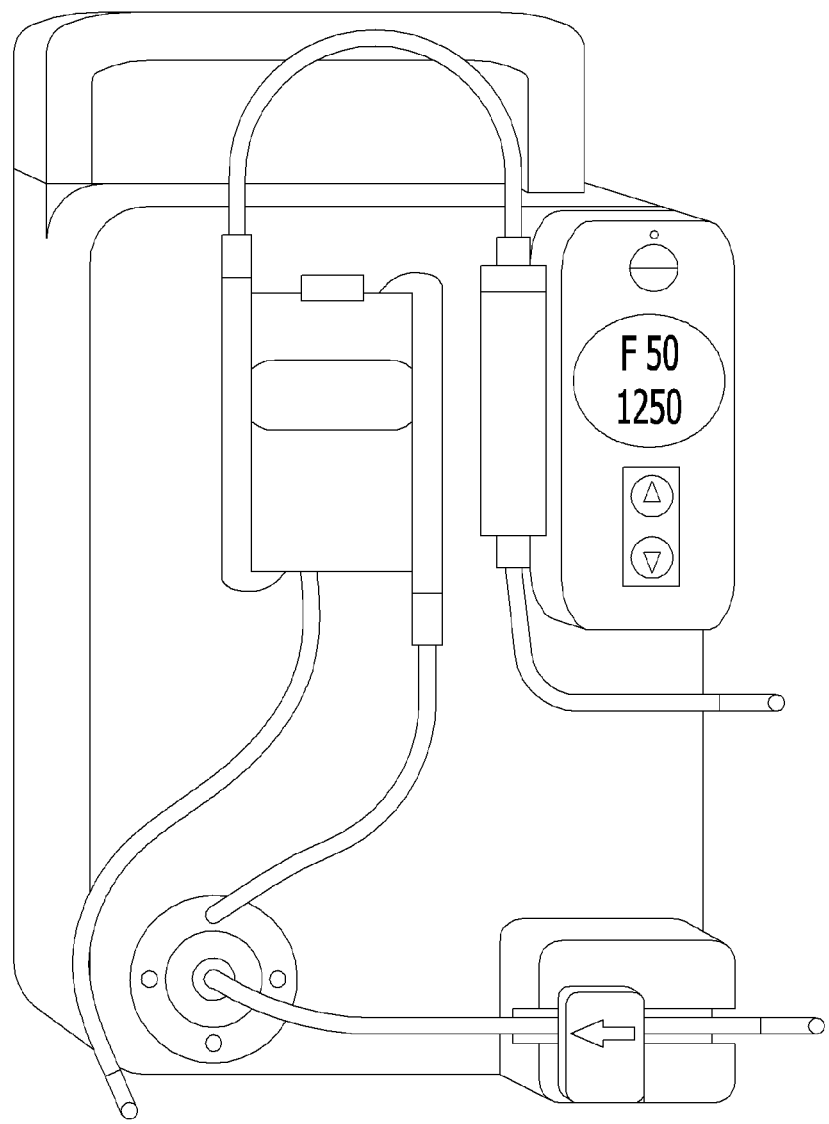
FIG. 3 is a structural diagram of a portable blood processing apparatus of the present invention.

FIGS. 1 and 2 are diagrams for schematically illustrating the configuration of an eco-friendly smart blood modulation device of the present invention. As illustrated in FIGS. 1 and 2, the present invention relates to a blood processing apparatus, which includes a blood supply unit 10, a centrifuge 20, a light irradiation unit 30, a filtering device 40, and a blood collection unit 50 and is characterized in that blood supplied from the blood supply unit 10 is introduced into the centrifuge 20 and centrifuged, the centrifuged blood is passed through a transparent tube provided in the light irradiation unit 30 while being irradiated with light, from the outside of the transparent tube 32, by a light irradiation device configured to include an infrared lamp with a wavelength of 830±5 nm, a red LED lamp with a wavelength of 635±6 nm, a blue LED lamp with a wavelength of 420±5 nm, a green LED lamp with a wavelength of 530±5 nm, a yellow LED lamp with a wavelength of 585±5 nm, and one or more UV lamps selected from among UV-A and UV-B lamps, and the blood irradiated with the light is filtered through the filtering device 40 and collected in the blood collection unit 50.

It should be noted that, in the blood processing apparatus of the present invention, each of the above-described components may be connected by a medical tube which allows blood to move, and an automated blood flow may be realized by a technique known in the art.

The blood supply unit 10 may consist of a container (e.g., blood bag) for accommodating blood collected from the human body as shown in FIG. 1 or may consist of a device for directly collecting blood from the human body as shown in FIG. 2.

The centrifuge 20 is a device for centrifuging blood, and may be used for the purpose of centrifuging blood to allow the blood to generate a photosensitizer by itself.

In addition, the blood processing apparatus of the present invention may be operated while administering a photosensitizer from an external source. Examples of the photosensitizer include Photofrin (Canada), PHOTOGEM (Russia), Photosan (Germany), 5-aminolevulinic acid (ALA) (Canada), which are porphyrin-based photosensitizers, and phthalocyanine, benzoporphyrin, Radachlorine, tin-etio-purpurin, ANTRIN, texaphyrin, Merocyanine 540, 8-methoxypsoralen (MOP), which are chlorine-based photosensitizers. Since the above materials are generated in the production of hemoglobin, it is also possible to induce the production of the materials in human blood itself by centrifugation or the like.

Among light types, LEDs such as laser LEDs, quantum LEDs (QLEDs), and organic LEDs (OLEDs) can be used. In the above-described light irradiation, light may be irradiated in the form of a continuous wave, a short wave, or a pulse wave.

In the blood processing apparatus of the present invention, the centrifugation may be carried out for 10 seconds to 3 minutes and more preferably 15 seconds to 1 minute in the centrifuge 20 rotating at a speed of 1,000 to 4,500 rpm and more preferably 2,500 to 3,500 rpm.

In addition, the light irradiation is preferably carried out for 10 seconds to 30 minutes and more preferably 1 minute to 10 minutes. In the above, the light irradiation time refers to the sum of time periods during which blood is simultaneously or sequentially exposed to, for example, all of infrared lamp light with a wavelength of 830±5 nm, red LED lamp light with a wavelength of 635±6 nm, blue LED lamp light with a wavelength of 420±5 nm, green LED lamp light with a wavelength of 530±5 nm, yellow LED lamp light with a wavelength of 585±5 nm, and UV lamp light irradiated from one or more selected from among UV-A and UV-B lamps.

In the present invention, the intensity and application time of centrifugation, light irradiation, filtering, oxygen supply, and the like may be appropriately adjusted according to the health condition of a patient and may be customized for the patient.

The blood processing apparatus of the present invention may additionally include an oxygen supply device 60 for supplying oxygen to the blood centrifuged by the centrifuge 20, as shown in FIG. 1 or FIG. 2.

In the blood processing apparatus of the present invention, the supply of oxygen carried out using the oxygen supply device 60 provides effects such as suppressing aging, removing toxins from the body, cleaning blood vessels, purifying blood, and the like.

The blood processing apparatus of the present invention may additionally include a nutrient injection unit 70 for injecting nutrients into the blood filtered by the filtering device 40.

In order to subject the blood primarily centrifuged by the centrifuge 20 to secondary centrifugation, the blood processing apparatus may additionally include one more centrifuge 20, as shown in FIGS. 1 and 2. When more than one centrifuge is provided as described above, the production of a photosensitizer can be promoted.

The first centrifuge and the second centrifuge are operated in accordance with the conditions described above.

In the blood processing apparatus of the present invention, the light irradiation unit 30 may be configured so that a transparent tube 32 passes through a light irradiation zone of the light irradiation device 31 in which an infrared lamp zone with a wavelength of 830±5 nm, a red LED lamp zone with a wavelength of 635±6 nm, a blue LED lamp zone with a wavelength of 420±5 nm, a green LED lamp zone with a wavelength of 530±5 nm, a yellow LED lamp zone with a wavelength of 585±5 nm, and one or more UV lamp zones selected from among UV-A and UV-B lamp zones are arranged.

The tube may be a transparent tube usable for medical purposes.

The light irradiation unit 30 may be configured so that the transparent tube 32 passes through the light irradiation zone of the light irradiation device 31 in which an infrared lamp with a wavelength of 830±5 nm, a red LED lamp with a wavelength of 635±6 nm, a blue LED lamp with a wavelength of 420±5 nm, a green LED lamp with a wavelength of 530±5 nm, a yellow LED lamp with a wavelength of 585±5 nm, and one or more UV lamps selected from among UV-A and UV-B lamps are alternately arranged.

The above-described alternating arrangement may be a regular arrangement or a random arrangement.

In the blood processing apparatus of the present invention, the transparent tube 32 may pass through the light irradiation zone in a zigzag manner.

The filtering device 40 is used for purifying blood through filtration, and one generally used in the art, such as for hemodialysis, may be used.

Figure 4:
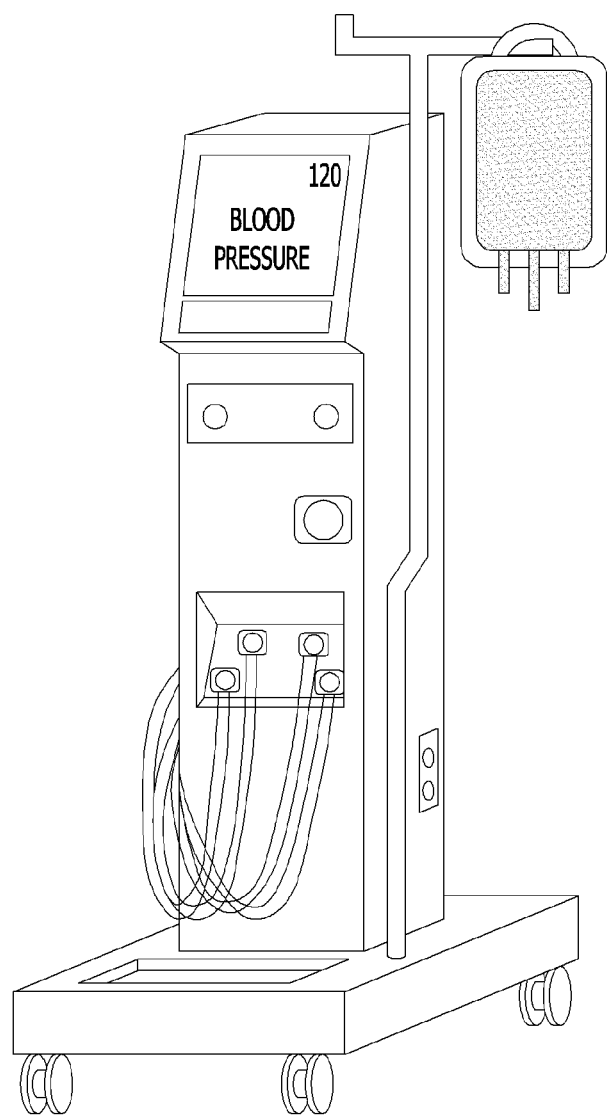
FIG. 4 is a structural diagram of a medium-sized blood processing apparatus of the present invention.
Figure 5A:
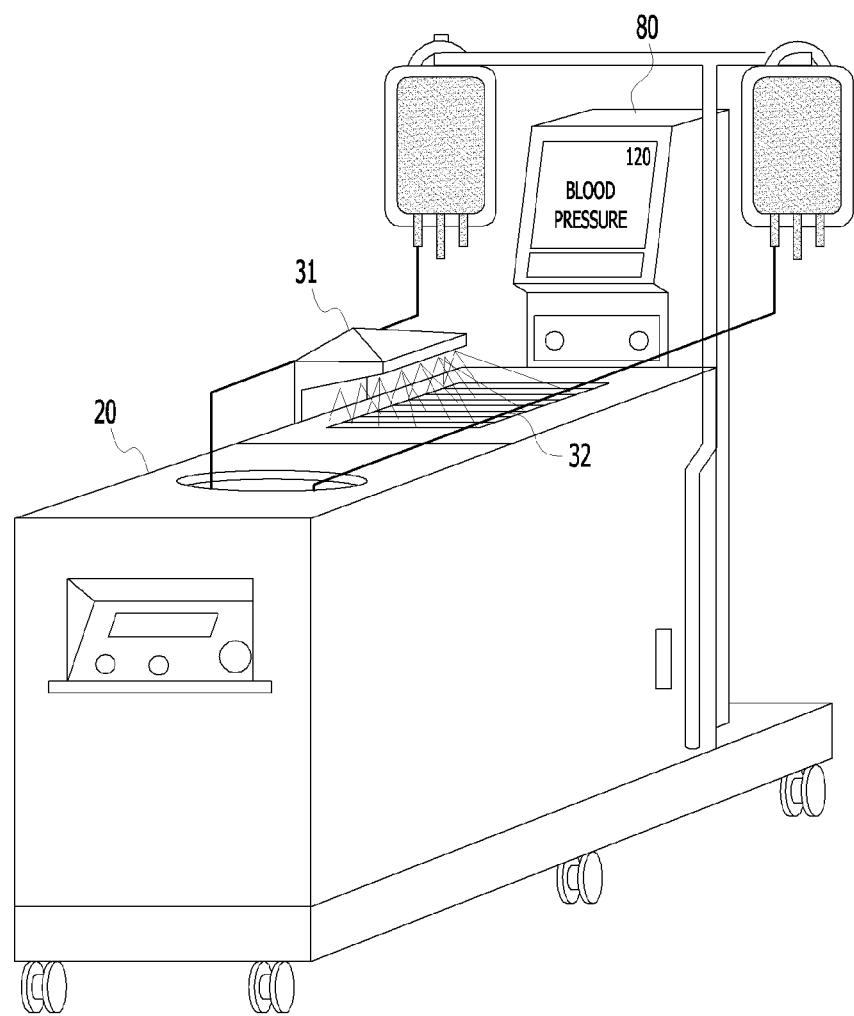
FIGS. 5A-5C show structural diagrams of a large-sized horizontal-type blood processing apparatus of the present invention.
Figure 5B:
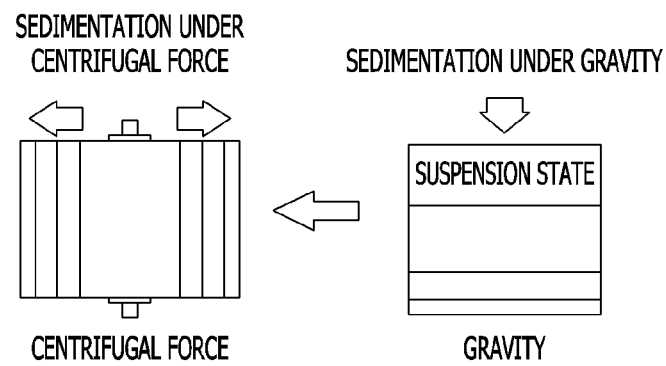
Figure 5C:
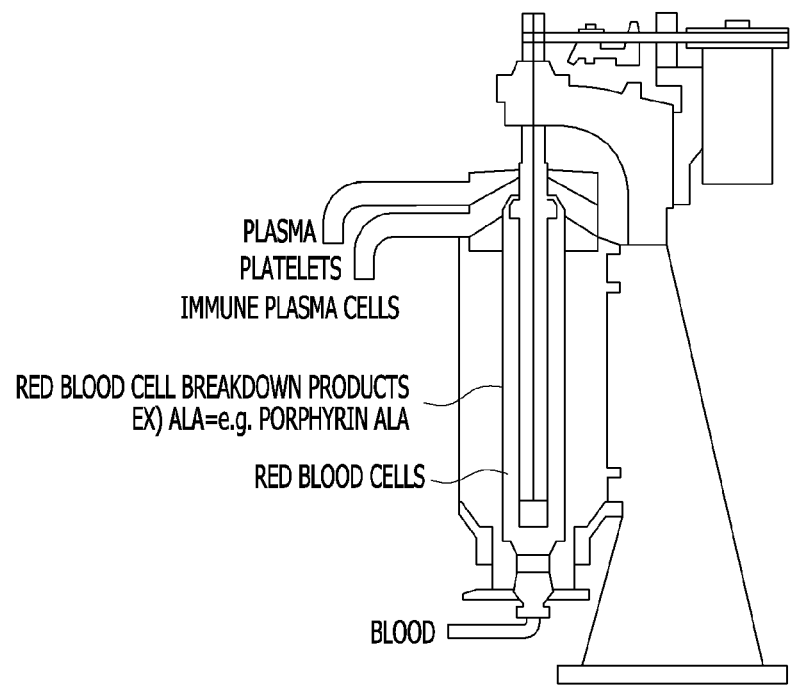
Figure 6A:
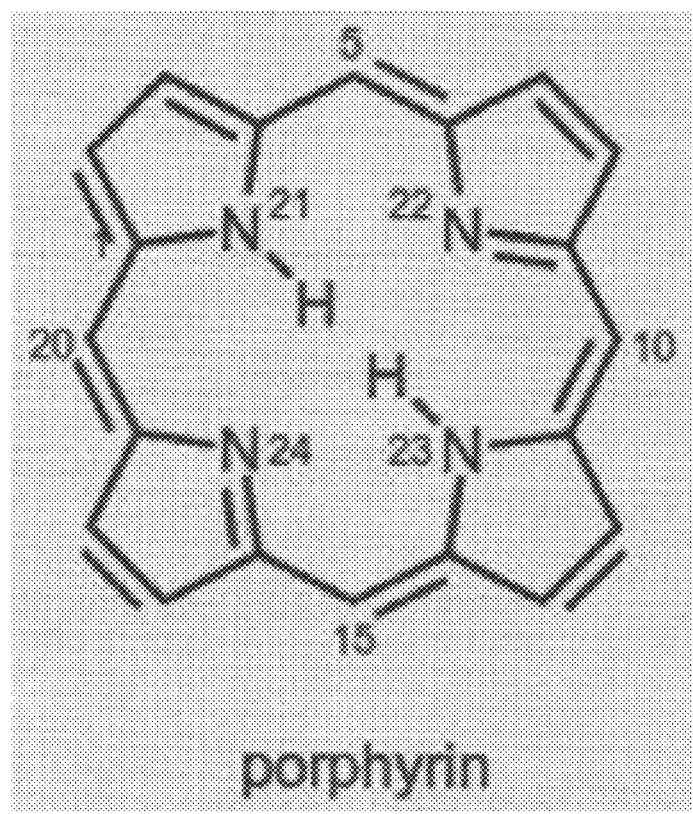
FIG. 6A shows a molecular formula of porphyrin.
Figure 6B:
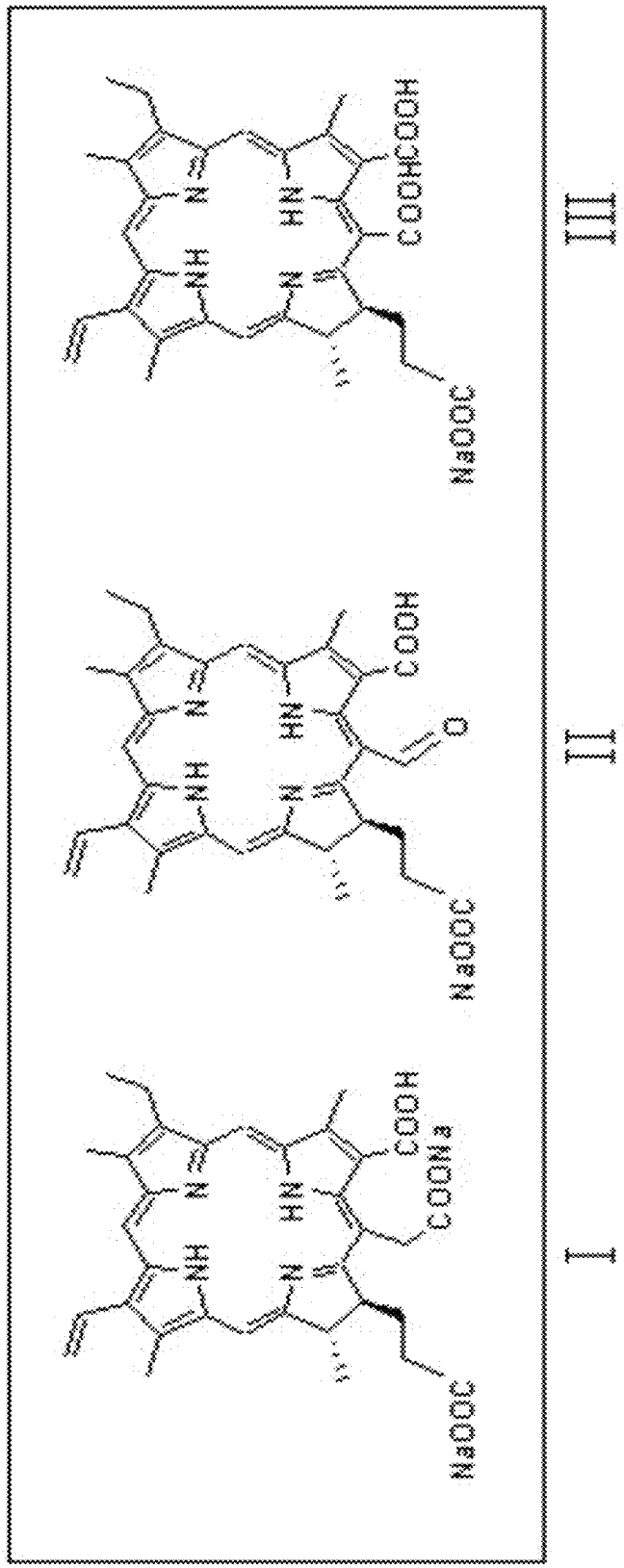
FIG. 6B shows molecular formulas of radachlorin.
Figure 6C:
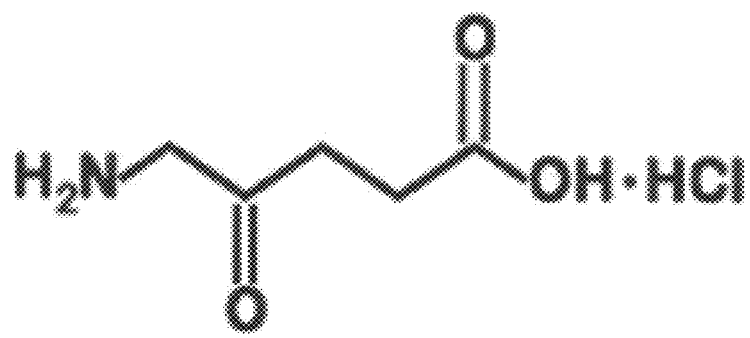
FIG. 6C shows a molecular formula of ALA.
Figure 6D:
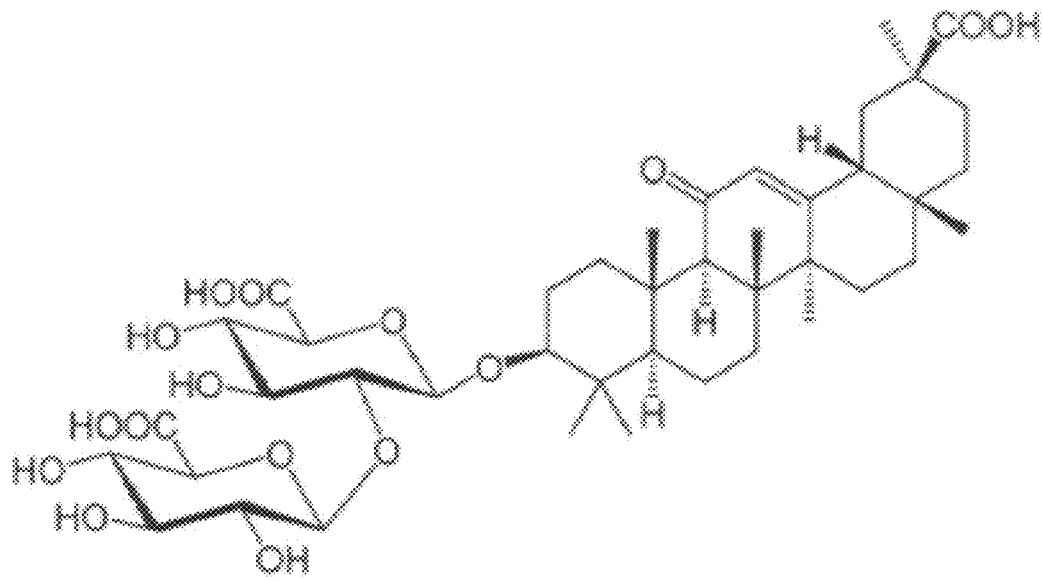
FIG. 6D shows a molecular formula of glycyrrhizin.
Figure 6E:
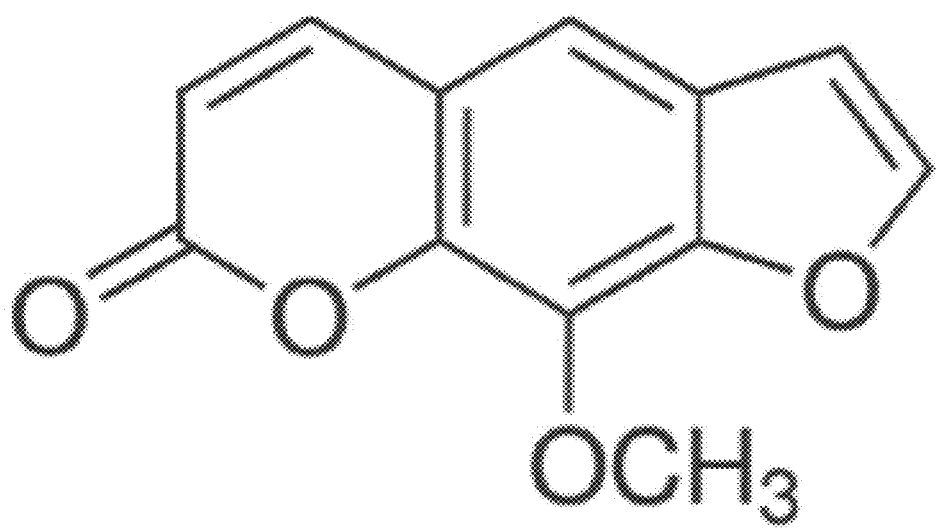
FIG. 6E shows a molecular formula of 8-methoxypsoralen.
Figure 6F:
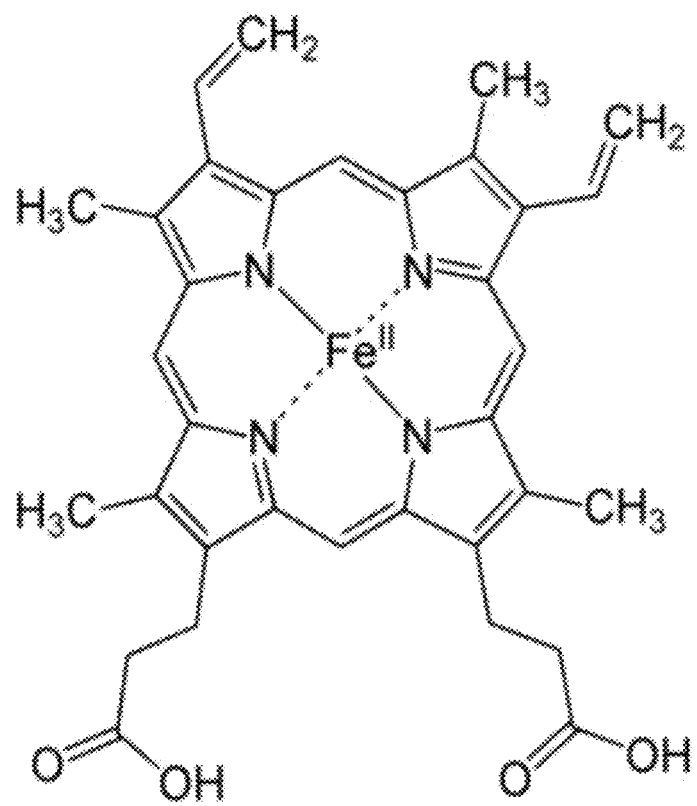
FIG. 6F shows a molecular formula of hemoglobin.
Figure 6G:
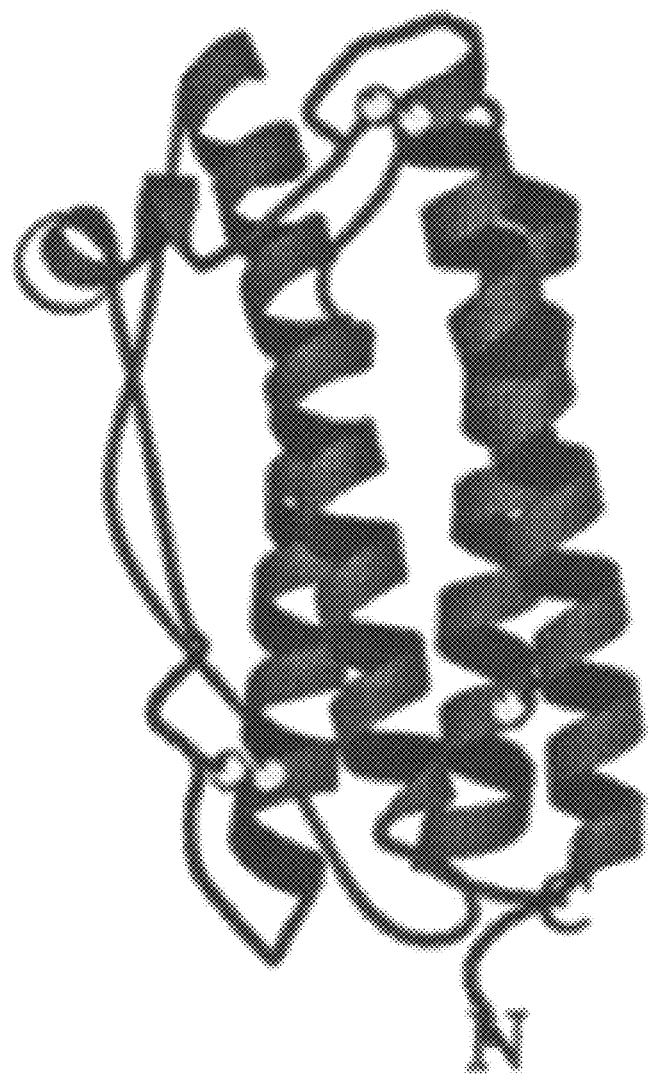
FIG. 6G shows a molecular formula of G-CSF.
Figure 7:
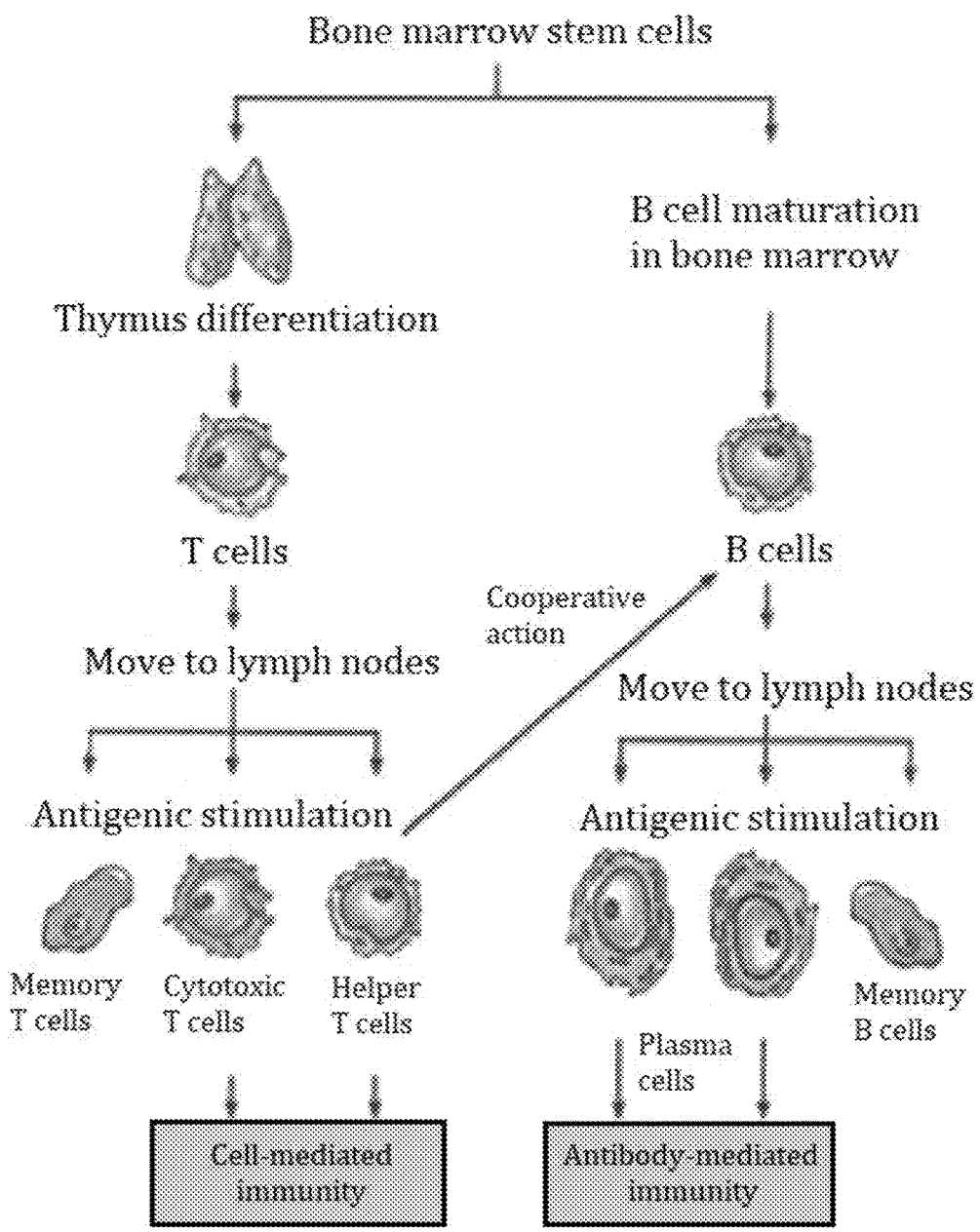
FIG. 7 shows the process relating to cell-mediated immunity and antibody-mediated immunity.

The blood processing apparatus of the present invention may additionally include a monitoring device and a monitoring sensor, such as a body temperature sensor, used for monitoring a patient's condition in conjunction with the monitoring device, as shown in FIGS. 4 and 5. The monitoring sensor may be provided in a form that can be attached to the human body.

In addition, the blood processing apparatus of the present invention may additionally include a sound wave generator and an ultrasonic generator. The installation position of the sound wave generator and the ultrasonic generator may be, for example, between the oxygen supply device and the light irradiation unit, but the present invention is not limited thereto. In addition, the blood processing apparatus of the present invention may additionally include a photocatalyst fixing unit for applying a photocatalyst to the blood being processed. The installation position of the photocatalyst fixing unit may be, for example, between the oxygen supply device and the light irradiation unit where it comes into contact with the blood, but the present invention is not limited thereto.

The blood processing apparatus of the present invention provides an effect of strengthening the immunity of blood. Furthermore, the blood processing apparatus of the present invention is applicable to target cell therapy for fighting cancer such as solid cancer and blood cancer, the remediation of autoimmunity, and the prevention and treatment of high blood pressure, heart disease, diabetes, lung disease, liver disease, gastrointestinal disease, musculoskeletal disease, Parkinson's disease, brain tumors, hydrocephalus, aging, hypoxia, Middle East respiratory syndrome (MERS), acquired immunodeficiency syndrome (AIDS), Ebola virus disease, and the like. In particular, with the blood processing apparatus of the present invention, anti-cancer stem cell exosomes can be obtained in an eco-friendly manner.

<Smart Biomodulator Source Technology Platform>

(HGF, IGF, EGF, Eotaxin, FGF-2 (bFGF), Flt-3 ligand, Fractalkine, GM-CSF, IFN-α2a, IFN-γ, IL-10, IL-12 (p40), IL-12 (p70), IL-13, IL-15, IL-17, IL-1a, IL-1B, IL-2, IL-3, IL-4, IL-5, IL-6, IL-7, IL-8, IL-9, IP-10, MCP-1, MIP-1a, MIP-1B, PDGF-AA, PDGF-BB, RANTES, sCD40L, TNF-α, TNF-β, TNG-α, VEGF, G-CSF, stem cells, double antibodies, CAR T, immune checkpoint inhibitors, immune anti-cancer drugs, immune modulator combination therapy, stem cell enhancement and in-vivo self-cultivation therapy and procedures, PIP, EIS, BIO COM, SCIO, GDV, qubits, quantum computing biology)

Hereinafter, the present invention will be described in more detail through Examples. However, the following Examples are for describing the present invention in more detail, and the scope of the present invention is not limited by the following Examples. The following Examples can be appropriately modified and changed by those skilled in the art within the scope of the present invention.

Example 1

Six-week-old specific pathogen-free (SPF) Sprague-Dawley (SD) rats were subjected to blood processing using the blood processing apparatus of the present invention.

That is, 3 ml of blood was collected from the SD rats once every three days and centrifuged for 20 seconds in a centrifuge rotating at a speed of 3,500 rpm, and after centrifugation was completed, the blood was supplied through a transparent tube while being irradiated for five minutes with light applied, from the outside of the transparent tube, by a light irradiation device in which an infrared lamp with a wavelength of 830±5 nm, a red LED lamp with a wavelength of 635±6 nm, a blue LED lamp with a wavelength of 420±5 nm, a green LED lamp with a wavelength of 530±5 nm, a yellow LED lamp with a wavelength of 585±5 nm, and a UV-B lamp were arranged in the order as written. After the light irradiation was completed, the blood was subsequently filtered using a filtering device and then injected back into the SD rats.

Example 2

The processes of Example 1 were repeated except that a process of supplying oxygen to blood using an oxygen blood device after centrifugation was completed and then supplying the blood to a transparent tube was additionally carried out.

Experimental Example 1: Acute Toxicity Test

The toxicity test was conducted using six-week old SPF SD rats. Three milliliters of blood was collected from five rats once every three days, processed using the blood processing apparatus of the present invention, and then injected back into the rats. For six weeks, the animals were monitored to determine whether they were dead or alive and evaluate clinical symptoms and body weight changes, and were subjected to hematological and hematobiochemical tests, and subsequently, an autopsy was performed to visually observe the abnormalities of tonic organs and thoracic organs.

The results of this test showed that none of the rats into which the blood processed using the blood processing apparatus of the present invention was injected back showed notable clinical symptoms or died, and according to the results of body weight change evaluation, hematological and hematobiochemical tests, and autopsy findings, no toxicity change was observed.

Experimental Example 2: In-Vivo Experiment for Evaluating Changes in Body Weight, Various Organs, and the Like Blood was collected from C57BL/6 mice in which immunodeficiency was induced in vivo and injected back after being processed by the blood processing apparatus of the present invention, and an experiment was conducted as follows by applying a method disclosed in a document to study how the body weight and various organs of the mice and the like were affected and changed (Ho J N, Kang E R, Yoon H G, Jeon H, Jun W, Watson R R, Lee J, Biosci. Biotechnol. Biochem. 2011 July; 75(7):1234-9).

2-1: Production of LP-BM5 Virus

A mixture of LP-BM5 MuLV virus, which is the murine AIDS (MAIDS) virus that induces the disruption of the immune system in mice by causing leukemia, was prepared from adult mice with a non-neoplastic lymphoproliferative disease.

Bone marrow stromal cells were isolated from virus-infected mice and propagated into cell lines containing the virus. Infection with a murine RNA tumor virus typically causes the enlargement of lymphoid organs such as the spleen and lymph nodes. In addition, the infection causes tremendous immune suppression in the host's response, reducing resistance to opportunistic pathogens or malignant neoplasms.

The gag of the BM5 ecotropic virus encodes a 65 kD polyprotein, whereas the BM5 defective virus encodes a smaller 60 kD protein and cannot induce MAIDS by itself because pol and env regions are usually missing. Therefore, it is known that MAIDS is induced when a mixture of the BM5 ecotropic virus and defective virus is injected into mice (Cook W J, Green K A, Obar J J, Green W R. J Virol Methods. 2003. March; 108(1):49-58).

Therefore, into SC-1 cells of the mice, LP-BM5 viral DNA made from adult mice with a non-neoplastic lymphoproliferative disease was injected so that viral particles were released from the cells into a culture medium.

2-2: Experimental Animals and Treatment

Four-week-old female C57BL/6 mice having a weight of about 20 g supplied from an animal breeding farm of Samtako Bio Korea were acclimated in a rodent breeding room for one week while monitoring general conditions during the acclimation period, and only healthy mice individuals were used for the experiment. The breeding environment was maintained under a temperature of 23±3° C., a humidity of 50±5%, and a light cycle of 12 hours.

The body weights of the animals determined to be healthy during the acclimation period were measured, and individuals having an approximate average body weight were selected and randomly grouped into a non-infection group of five mice, an infection group of five mice, and an experimental group of five mice, to which the blood processing apparatus of the present invention was applied. In order to create an immune destruction animal model, LP-BM5, which is a virus that disrupts the immune system in mice, was obtained from a culture medium of SC-1 cells (NIH, 1215) and intraperitoneally injected twice into C57BL/6 mice, which is a type sensitive to pathogens, to infect the mice with the virus and disrupt immunity by causing leukemia. Subsequently, the mice infected with the virus and whose immune system was disrupted were subjected to blood processing for six weeks, during which time 3 ml of blood was collected once every three days and then injected back into the mice after processing with the blood processing apparatus of the present invention. The amount of diet and body weights of the mice were measured once every week, and after the six weeks, the mice were sacrificed. The experimental results are shown as average values for each group.

TABLE 1

| Group | Induction of immune destruction | Provided diet |
|---|---|---|
| Wild type | x | AIN 93G |
| Infection | o | AIN 93G |
| Experimental group subjected to blood processing by blood processing apparatus of the present invention | o | AIN 93G |

2-3: Findings on Anatomical Changes and Organ Weight Changes
2-3-1: Change in Lymph Node Weight In this experiment, it was difficult to visually observe the lymph nodes in the non-infection group, but in the infection group, the size of the lymph nodes increased and the weight was 4.55±0.21 g. On the other hand, in the experimental group in which 3 ml of blood was processed once every three days using the blood processing apparatus of the present invention for a total of six weeks, the weight of the lymph nodes was 2.88±0.33 g. Therefore, it can be seen that the weight of the lymph nodes in the infection group was significantly decreased.

2-3-2: Change in Spleen Weight

In this experiment, the weight of the spleen was 0.07±0.01 g in the normal group and 0.82±0.12 g in the infection group, and it can be seen that the weight of the spleen significantly increased in the infection group. This result shows that infection with the LP-BMS retrovirus was normally achieved and there was no effect by pathogens other than LP-BM5.

It can be seen that in the experimental group in which 3 ml of blood was processed once every three days using the blood processing apparatus of the present invention for a total of six weeks, the weight of the spleen was 0.59±0.11 g, which is significantly decreased as compared to the infection group.

2-4: Body Weight Change and Dietary Efficiency

The dietary intake of the experimental animals did not have statistical significance in all groups, and it is determined that the result confirms that all experimental data did not reflect a difference in dietary intake rates. An increase in body weight was more significant in the infection group than in the non-infection group, and it is determined that this is because, in the case of infection with the LP-BMS retrovirus, edema is common, and a body weight increases due to inflammatory reactions in the body and the like. In addition, it can also be seen that in the experimental group, in which 3 ml of blood was processed once every three days using the blood processing apparatus of the present invention for a total of six weeks, a significant increase in body weight as compared to the non-infection group but a significant decrease in body weight as compared to the infection group was exhibited.

TABLE 2

| Group | Dietary intake amount (g/day) | Increase in body weight (g/4 weeks) |
|---|---|---|
| Wild type | 2.45 ± 0.12 | 2.21 ± 0.32 |
| Infection | 2.21 ± 0.19 | 3.62 ± 0.21 |
| Experimental group subjected to blood processing by blood processing apparatus of the present invention | 2.33 ± 0.32 | 3.01 ± 0.13 |

Experimental Example 3: In-Vivo Experiment for Evaluating Effect on Cytokine Production Ability of Splenocytes In order to evaluate the effect of blood processing by the blood processing apparatus of the present invention on the expression of cytokines in splenocytes, an experiment was conducted as follows by applying a method disclosed in a document (Ho J N, Kang E R, Yoon H G, Jeon H, Jun W, Watson R R, Lee J, Biosci. Biotechnol. Biochem. 2011 July; 75(7):1234-9).

3-1: Measurement of Cytokine Production Ability of Splenocytes (IL-2, -4, -6, -10, -12, -15, TNF-α, IFN-γ)

For the isolation and cultivation of splenocytes, the mice being tested were sacrificed with cervical dislocation, the abdomen was sterilized with 70% ethanol, and the spleen was removed aseptically and then homogenized with a sterilized homogenizer (Kinematica, PT1200B). Subsequently, a 40-mesh mesh was placed on a 50 ml conical tube (SPL Life Sciences, Korea, 50050). After the mesh was wetted with a RPMI 1640 (HyClone, USA, SH30027.01) culture solution including 10% fetal bovine serum (HyClone, USA, SH30919.03) and 1% penicillin (HyClone, USA, SV30010), the homogenized spleen was passed through the mesh and then washed twice with RPMI 1640.

In order to remove red blood cells, the red blood cells were destroyed in a solution in which equal amounts of a red blood cell lysis buffer (Sigma-Aldrich, USA, RNBC5060) and Dulbecco's phosphate-buffered saline (DPBS) (Welgene, Korea, LB001-02) were mixed, and the resultant was washed twice with a PBS solution in the same manner and, after determining cell viability with a trypan blue stain (Gibco, USA, lot #1129155) exclusion test, seeded in each well of a 96-well plate at a concentration of 1×10⁶ cells/200 µl. Subsequently, to the 96-well plate where seeding had been performed, concanavalin A (ConA) or lipopolysaccharide (LPS) was added at a concentration of 5 µg/mL as shown in Table 3 below, and incubation was performed for a time as shown in Table 3 below, and the amount of cytokines produced was measured using a Duoset sandwich ELISA Mouse kit (R&D Systems, USA) (IL-2: R&D Systems, USA, DY402, IL-4: R&D Systems, USA, DY404, IL-6: R&D Systems, USA, DY406, IL-10: R&D Systems, USA, DY417, IL-12: R&D Systems, USA, DY419, IL-15: R&D Systems, USA, DY447, TNF-α: R&D Systems, USA, DY410, IFN-γ: R&D Systems, USA, DY485).

TABLE 3

| Cytokine | Mitogen | Incubation time |
|---|---|---|
| IL-2 | ConA | 24 hrs |
| IL-4 | ConA | 24 hrs |
| IL-6 | LPS | 24 hrs |
| IL-10 | ConA | 24 hrs |
| IL-12 | LPS | 48 hrs |
| IL-15 | LPS | 48 hrs |
| TNF-α | LPS | 24 hrs |
| TNF-α | ConA | 72 hrs |

A primary antibody specialized for the measurement of each type of cytokine was diluted in PBS in an ELISA 96-well plate (Costar, USA, 3590), dispensed at 100 µl, and treated for one day. On the next day, after washing the primary antibody with a washing buffer (PBST; 0.05% Tween 20 (USB Corporation, USA, Lot #123229) in PBS), the plate was washed with an assay buffer (1% bovine serum albumin (BSA; Sigma-Aldrich, USA, Lot #99H1081) in PBS (IL-4, -6, -10, -12, -15, TNF-α) or 0.1% BSA in Tris-buffered saline with Tween 20 (TBST; IL-2, IFN-γ)) for two hours to fill spaces where the antibodies were not attached and then washed with a washing buffer. 100 µl of a solution for a standard curve and 100 µl of a culture solution of the splenocytes seeded in the above were added to each well and reacted for two hours, and after the reaction was completed, the plate was washed with a washing buffer, a secondary antibody diluted in an assay buffer was prepared and dispensed at 100 µl in each well and treated for two hours. When this process was completed, the plate was washed using a washing buffer, and a reaction was induced by adding 100 µl of a substrate reagent (R&D Systems, USA, DY999) capable of helping color development, and by measuring absorbance at 570 nm using an ELISA reader (VERSAMAXSL-20, Molecular Devices, Korea) and using a standard curve, the amount of cytokines produced in cells was calculated.

3-1-1: Regulation of Expression of IL-2 Cytokine

It can be seen that IL-2 expression was 6519.64±31.29 pg/mL in the normal group but significantly reduced to 61.36±10.75 pg/mL in the infection group. It can be seen that in the experimental group in which 3 ml of blood was processed once every three days using the blood processing apparatus of the present invention for a total of six weeks, IL-2 expression was 177.44±11.50 pg/mL, and the extent to which IL-2 expression was decreased was significantly smaller than that of the infection group.

3-1-2: Expression of IFN-γ Cytokine

In the present experiment, it can be seen that IFN-γ expression was 792.08±11.22 pg/mL and significantly highest in the normal group and significantly decreased to 152.5±11.72 pg/mL in the infection group. It can be seen that in the experimental group in which 3 ml of blood was processed once every three days using the blood processing apparatus of the present invention for a total of six weeks, IFN-γ expression was 642.12±10.11 pg/mL, and the extent to which IFN-γ expression was decreased was significantly smaller than that of the infection group.

3-1-3: Expression of IL-12

In the present experiment, it can be seen that IL-12 expression was significantly reduced in the infection group as compared to the normal group. In the experimental group in which 3 ml of blood was processed once every three days using the blood processing apparatus of the present invention for a total of six weeks, IL-12 expression was not significantly different from that of the normal group.

3-1-4: Expression of IL-15

In the present experiment, it can be seen that an IL-15 expression level was 45.22±3.02 pg/mL in the normal group but significantly reduced to 32.81±1.34 pg/mL in the infection group. In the experimental group in which 3 ml of blood was processed once every three days using the blood processing apparatus of the present invention for a total of six weeks, IL-15 expression was 43.55±3.21 pg/mL, which was not significantly different from that of the normal group.

3-1-5: Expression of IL-4

In the present experiment, it can be seen that IL-4 expression was significantly increased to 133.11±6.15 pg/mL in the infection group as compared to 8.44±2.74 pg/mL in the normal group. It can be seen that in the experimental group in which 3 ml of blood was processed once every three days using the blood processing apparatus of the present invention for a total of six weeks, IL-4 expression was 15.50±4.11 pg/mL, which was significantly reduced as compared to the infection group.

3-1-6: Expression of IL-6

In the present experiment, it can be seen that IL-6 expression was significantly increased in the infection group as compared to the normal group. It can be seen that in the experimental group in which 3 ml of blood was processed once every three days using the blood processing apparatus of the present invention for a total of six weeks, IL-6 expression was significantly reduced as compared to the infection group.

3-1-7: Expression of IL-10

In the present experiment, IL-10 expression level was 32.64±3.71 pg/mL in the normal group but significantly increased to 641.11±33.51 pg/mL in the infection group. It can be seen that in the experimental group in which 3 ml of blood was processed once every three days using the blood processing apparatus of the present invention for a total of six weeks, an IL-10 expression level was 325.71±11.43 pg/mL, which was significantly reduced as compared to the infection group.

3-1-8: Expression of TNF-α

In the present experiment, TNF-α expression was 322.31±21.36 pg/mL in the infection group, which was significantly increased as compared to 46.34±5.55 pg/mL in the normal group. It can be seen that in the experimental group in which 3 ml of blood was processed once every three days using the blood processing apparatus of the present invention for a total of six weeks, TNF-α expression was 182.28±2.05 pg/mL, which was significantly reduced as compared to the infection group.

Experimental Example 4: In-Vivo Experiment for Evaluating Effect on T/B Cell Proliferation Ability in Splenocytes In order to evaluate the effect of samples of the above-described Examples on T/B cell proliferation ability in splenocytes, an experiment was conducted as follows by applying a method disclosed in a document (Ho J N, Kang E R, Yoon H G, Jeon H, Jun W, Watson R R, Lee J, Biosci. Biotechnol. Biochem. 2011 July; 75(7):1234-9).

4-1: Measurement of T/B Cell Proliferation Ability

Mice from which blood was collected were anesthetized and dissected, and the spleen was removed and washed with PBS and then placed on a 0.45 cell strainer (BD Falcon, USA, REF352340) to grind the tissue. The cells were collected in an RPMI 1640 medium (Hyclone, USA, Cat #SH30027.01) including 10% FBS, centrifuged, reacted for one minute by adding a red blood cell lysis buffer (Sigma-Aldrich, USA, Lot #RNBC5060), and then further centrifuged twice. The resultant was treated with a trypan blue dye (Gibco, lot #1129155) to stain cells, and the cells were counted, added to a 96-well plate at a concentration of $1\times10^7$ cells/mL, and were treated with 5 µg/ml LPS (Sigma-Aldrich, USA, Lot #032M4082v) and 5 µg/ml ConA (Sigma-Aldrich, USA, Lot #090M8703v) and incubated for 48 hours under the conditions of 37° C. and 5% $CO_2$. Subsequently, 10 µl aliquots of EZ-CyTox (Deilab Inc., Korea, DLS1212) were dispensed, and incubation was performed for four hours, and absorbance was measured at 450 nm using an ELISA reader (VERSAMAXSL-20, Molecular Devices, Korea).

4-2: Measurement of T/B Cell Proliferative Response 4-2-1: Measurement of T Cell Proliferative Response to Mitogen It can be seen that when the T cell proliferation ability of the normal group was assumed to be 100%, a significantly decreased proliferation ability of 37.51±22.02% as compared to that of the normal group was exhibited in the infection group infected with LP-BMS retrovirus. It can be seen that in the experimental group in which 3 ml of blood was processed once every three days using the blood processing apparatus of the present invention for a total of six weeks, a significantly increased T cell proliferation ability of 77.45±3.51% as compared to that of the infection group was exhibited.

4-2-2: Measurement of B Cell Proliferative Response to Mitogen

In the present experiment, when the B cell proliferation ability of the normal group was assumed to be 100%, a significantly decreased proliferation ability of 38.41±4.21% was exhibited in the infection group. It can be seen that in the experimental group in which 3 ml of blood was processed once every three days using the blood processing apparatus of the present invention for a total of six weeks, a significantly increased B cell proliferation ability of 71.29±5.12% as compared to that of the infection group was exhibited.

An eco-friendly smart blood modulation device of the present invention provides an effect of safely and effectively improving the immune function of blood.

In addition, the eco-friendly smart blood modulation device of the present invention can be useful for target cell therapy for fighting cancer such as solid cancer and blood cancer, the remediation of autoimmunity, and the prevention and treatment of heart disease, diabetes, lung disease, liver disease, gastrointestinal disease, musculoskeletal disease, Parkinson's disease, brain tumors, hydrocephalus, aging, hypoxia, MERS, AIDS, Ebola virus disease, and the like by improving immune function at the blood level.

What is claimed is:

1. A blood processing apparatus comprising a blood supply unit, a centrifuge, a light irradiation unit, a filtering device, and a blood collection unit,
    wherein blood supplied from the blood supply unit is introduced into the centrifuge and centrifuged, the centrifuged blood is passed through a transparent tube provided in the light irradiation unit while being irradiated with light applied, from the outside of the transparent tube, by a light irradiation device configured to include an infrared lamp with a wavelength of 830±5 nm, a red light-emitting diode (LED) lamp with a wavelength of 635±6 nm, a blue LED lamp with a wavelength of 420±5 nm, a green LED lamp with a wavelength of 530±5 nm, a yellow LED lamp with a wavelength of 585±5 nm, and one or more ultraviolet (UV) lamps selected from among UV-A and UV-B lamps, and the blood irradiated with the light is filtered using the filtering device and collected in the blood collection unit,
    the blood processing apparatus additionally includes an oxygen supply device configured to supply oxygen to the blood centrifuged by the centrifuge,
    the blood processing apparatus additionally includes a nutrient injection unit configured to inject nutrients into the blood filtered using the filtering device,
    the blood processing apparatus additionally includes an ultrasonic generator and a photocatalyst fixing unit between the oxygen supply device and the light irradiation unit,
    the light irradiation unit is configured so that the transparent tube passes through a light irradiation zone of the light irradiation device in which an infrared lamp zone with a wavelength of 830±5 nm, a red LED lamp zone with a wavelength of 635±6 nm, a blue LED lamp zone with a wavelength of 420±5 nm, a green LED lamp zone with a wavelength of 530±5 nm, a yellow LED lamp zone with a wavelength of 585±5 nm, and one or more UV lamp zones selected from among UV-A and UV-B lamp zones are sequentially arranged,
    the centrifuge is configured to allow the blood to generate a photosensitizer, and
    the transparent tube is configured to pass through the light irradiation zone in a zigzag manner.

2. The blood processing apparatus of claim 1, comprising, in addition to the centrifuge, one more centrifuge configured to further centrifuge the centrifuged blood.

* * * * *